(12) United States Patent
Clement

(10) Patent No.: US 11,406,545 B2
(45) Date of Patent: Aug. 9, 2022

(54) FEMININE PRODUCT DISPENSING ASSEMBLY

(71) Applicant: Cassandra Clement, Reedley, CA (US)

(72) Inventor: Cassandra Clement, Reedley, CA (US)

( * ) Notice: Subject to any disclaimer, the term of this patent is extended or adjusted under 35 U.S.C. 154(b) by 281 days.

(21) Appl. No.: 16/862,889

(22) Filed: Apr. 30, 2020

(65) Prior Publication Data

US 2021/0338495 A1 Nov. 4, 2021

(51) Int. Cl.
*A61F 15/00* (2006.01)
*A61F 13/472* (2006.01)
*A61F 13/551* (2006.01)

(52) U.S. Cl.
CPC .......... *A61F 15/002* (2013.01); *A61F 13/472* (2013.01); *A61F 13/55145* (2013.01); *A61F 2013/55195* (2013.01)

(58) Field of Classification Search
CPC .................. A61F 15/002; A61F 13/472; A61F 13/55145; A61F 2013/55195; A61F 15/003
USPC ....... 206/581, 570, 229, 233, 438, 440, 223, 206/822, 823, 457; D9/624
See application file for complete search history.

(56) References Cited

U.S. PATENT DOCUMENTS

| | | | |
|---|---|---|---|
| 649,717 A | 5/1900 | Browne | |
| 758,735 A | 5/1904 | Boileau | |
| 3,307,687 A * | 3/1967 | Steinman | B65D 5/16 206/229 |
| D255,214 S * | 6/1980 | Creighton, Jr. | D9/624 |
| 5,020,673 A | 6/1991 | Adams | |
| 5,579,916 A | 12/1996 | Manko | |
| 5,988,386 A * | 11/1999 | Morrow | A61F 13/84 604/15 |
| 6,068,118 A | 5/2000 | Calloway | |
| 6,393,614 B1 * | 5/2002 | Eichelbaum | A41D 19/002 2/160 |
| 6,612,056 B1 * | 9/2003 | Thomas, II | G09F 21/02 40/586 |
| 7,147,129 B1 * | 12/2006 | Menefield | A61F 6/005 206/440 |
| 7,832,555 B2 * | 11/2010 | Flannery | A47K 10/421 206/229 |
| D649,717 S | 11/2011 | Chorne | |
| 8,424,489 B2 * | 4/2013 | Desrosiers | A01K 5/0114 119/61.5 |

(Continued)

FOREIGN PATENT DOCUMENTS

WO WO0217844 3/2002

*Primary Examiner* — J. Gregory Pickett
*Assistant Examiner* — Jenine Pagan

(57) ABSTRACT

A feminine product dispensing assembly includes a housing that has a central portion structured to resemble the palm of a human hand and a plurality of finger portions each structured to resemble fingers of a human hand. The central portion has an opening extending into an interior of the central portion for storing toilet paper and toilet covers and each of the finger portions has a tampon positioned therein for storage. A plurality of lids is each hingedly coupled to a respective one of the finger portions to retain the tampon in the respective finger portion. A magnet is coupled to the housing to magnetically engage a ferromagnetic support surface. A hook is coupled to and extends downwardly from the central portion for having an object suspended thereon for storage.

8 Claims, 5 Drawing Sheets

(56) References Cited

U.S. PATENT DOCUMENTS

| | | | |
|---|---|---|---|
| D691,853 S * | 10/2013 | Gilmour | ................. D9/601 |
| 8,899,418 B2 | 12/2014 | Francis | |
| D758,735 S | 6/2016 | Hernandez | |
| 2003/0136704 A1 | 7/2003 | Burgess | |
| 2010/0122709 A1 | 5/2010 | Janatpour | |

* cited by examiner

FEMININE PRODUCT DISPENSING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to dispensing devices and more particularly pertains to a new dispensing device for storing and dispensing feminine hygiene products in a public bathroom.

(2) Description of Related Art Including Information Disclosed Under 37 CFR 1.97 and 1.98

The prior art relates to dispensing devices. The prior art discloses a feminine hygiene product storage device that includes a plurality of foldable panels and pockets on the panels. Additionally, the prior art discloses a feminine hygiene product case that includes zippers and straps for securing feminine hygiene products. The prior art also discloses a toilet paper caddy for storing a roll of toilet paper in a case and that also includes a radio. The prior art discloses a tampon storage bag that has a plurality of elongate chambers integrated therein for storing tampons.

BRIEF SUMMARY OF THE INVENTION

An embodiment of the disclosure meets the needs presented above by generally comprising a housing that has a central portion structured to resemble the palm of a human hand and a plurality of finger portions each structured to resemble fingers of a human hand. The central portion has an opening extending into an interior of the central portion for storing toilet paper and toilet covers and each of the finger portions has a tampon positioned therein for storage. A plurality of lids is each hingedly coupled to a respective one of the finger portions to retain the tampon in the respective finger portion. A magnet is coupled to the housing to magnetically engage a ferromagnetic support surface. A hook is coupled to and extends downwardly from the central portion for having an object suspended thereon for storage.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
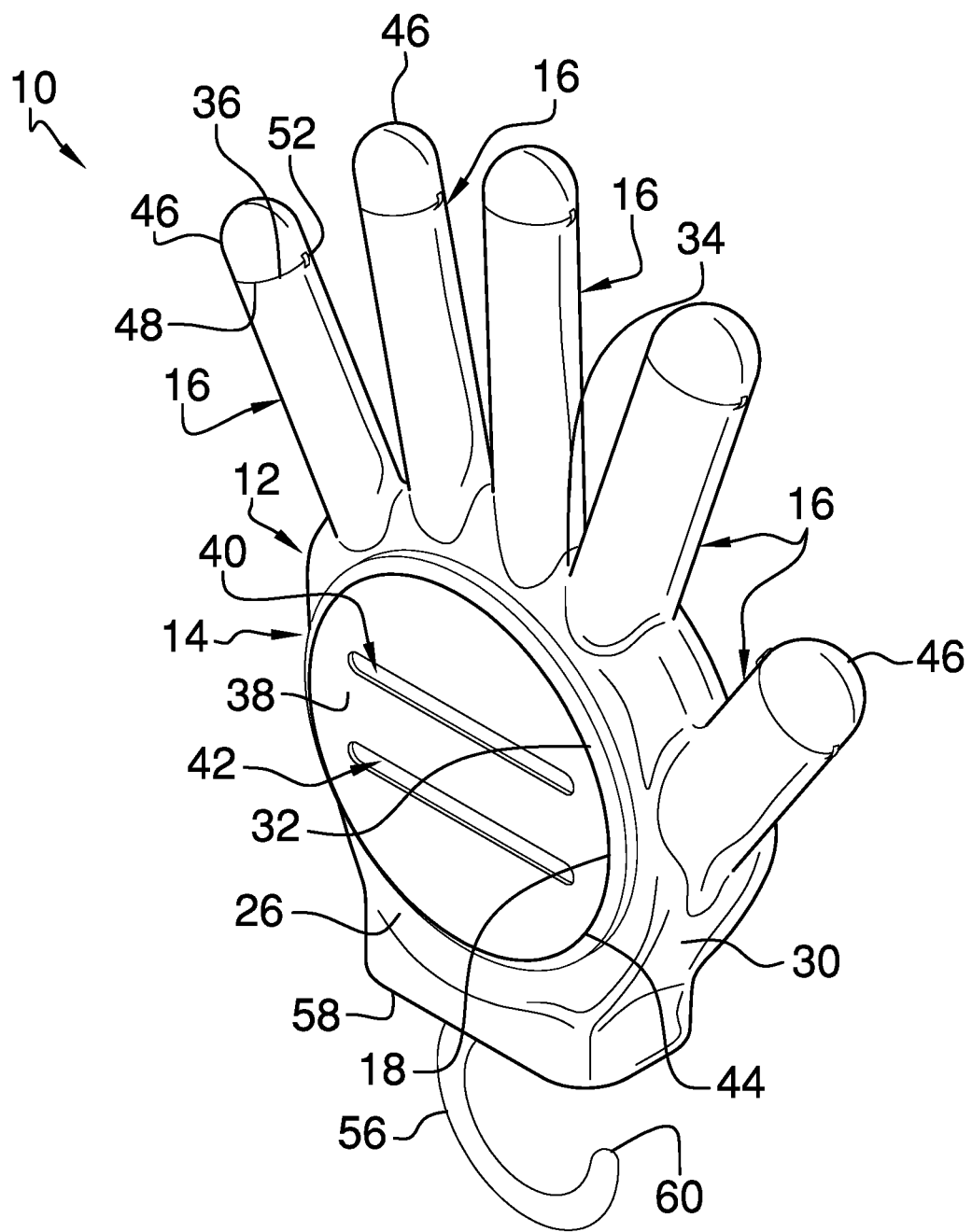
FIG. 1 is a front perspective view of a feminine product dispensing assembly according to an embodiment of the disclosure.
Figure 2:
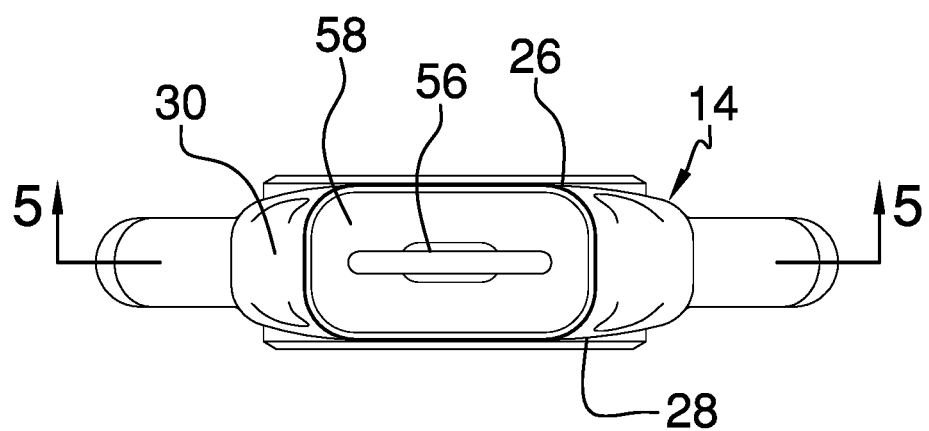
FIG. 2 is a bottom view of an embodiment of the disclosure.
Figure 3:
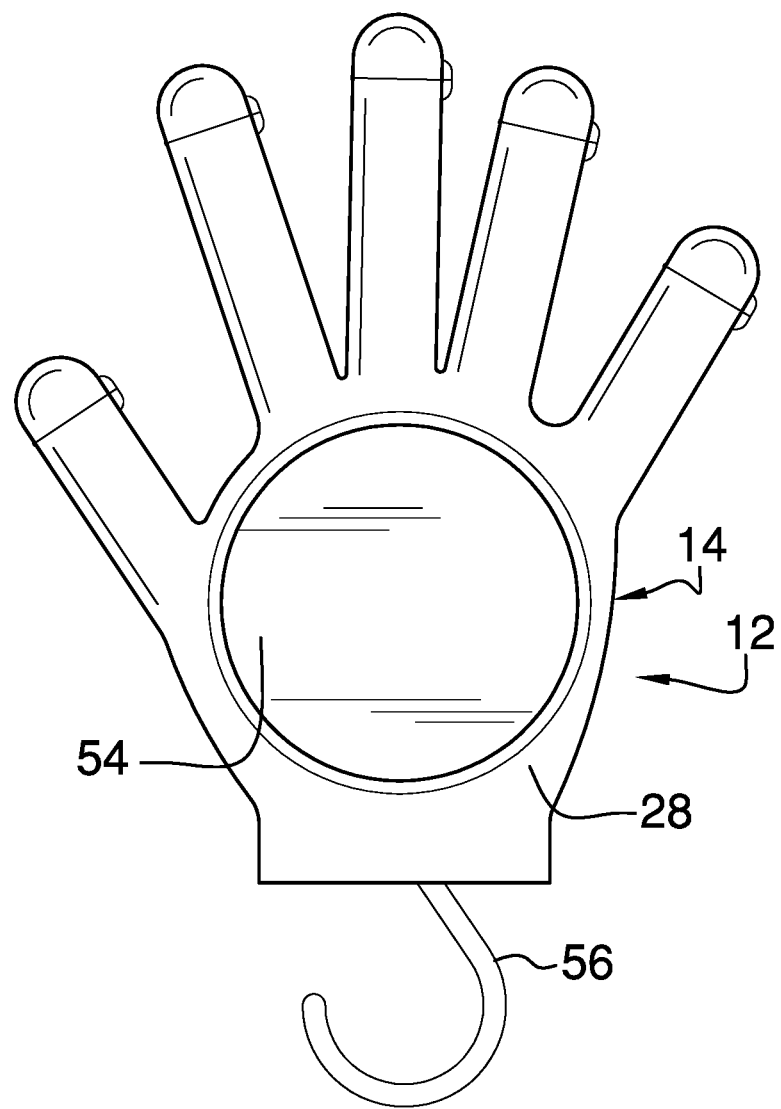
FIG. 3 is a back view of an embodiment of the disclosure.
Figure 4:
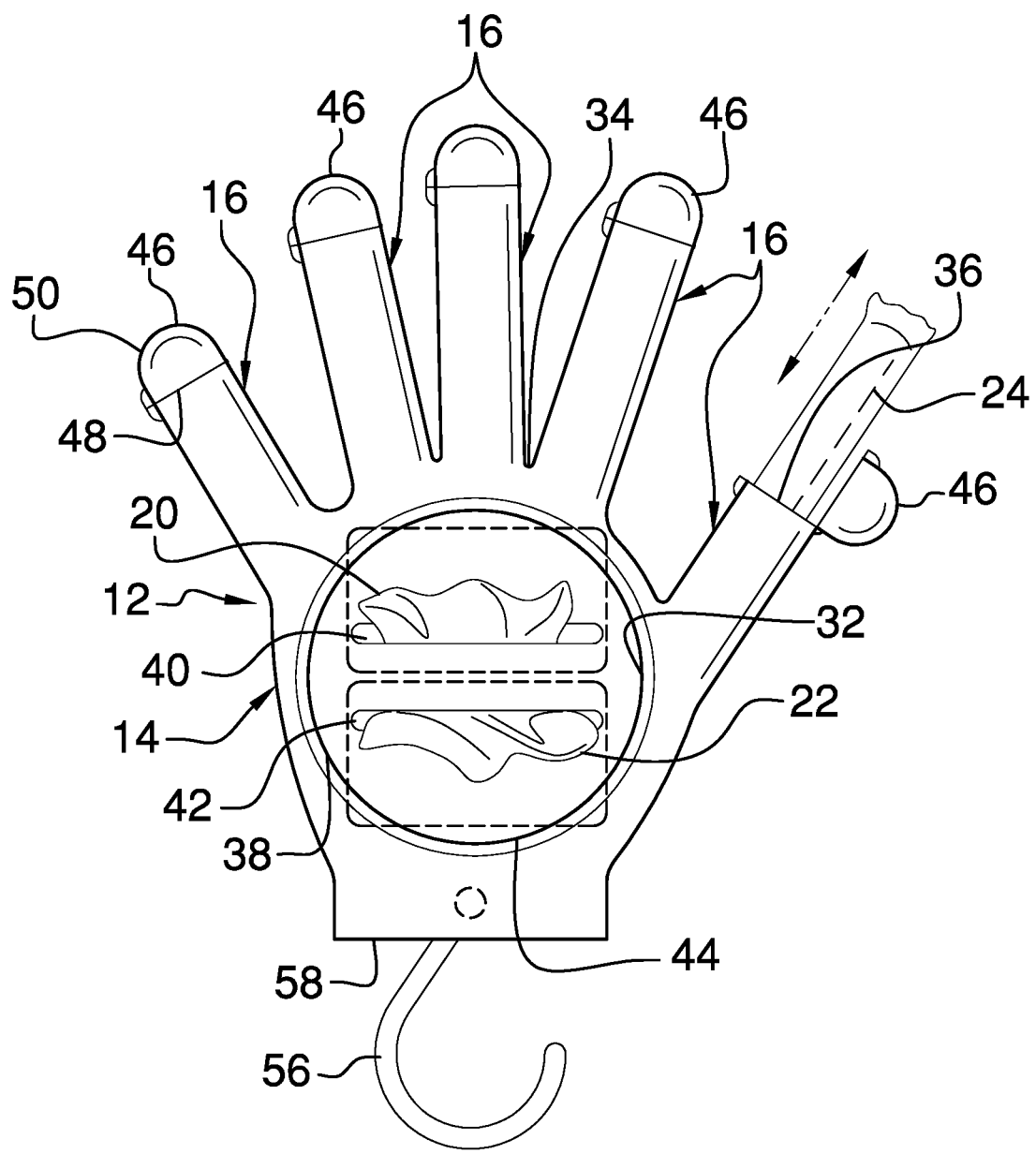
FIG. 4 is a front phantom view of an embodiment of the disclosure.
Figure 5:
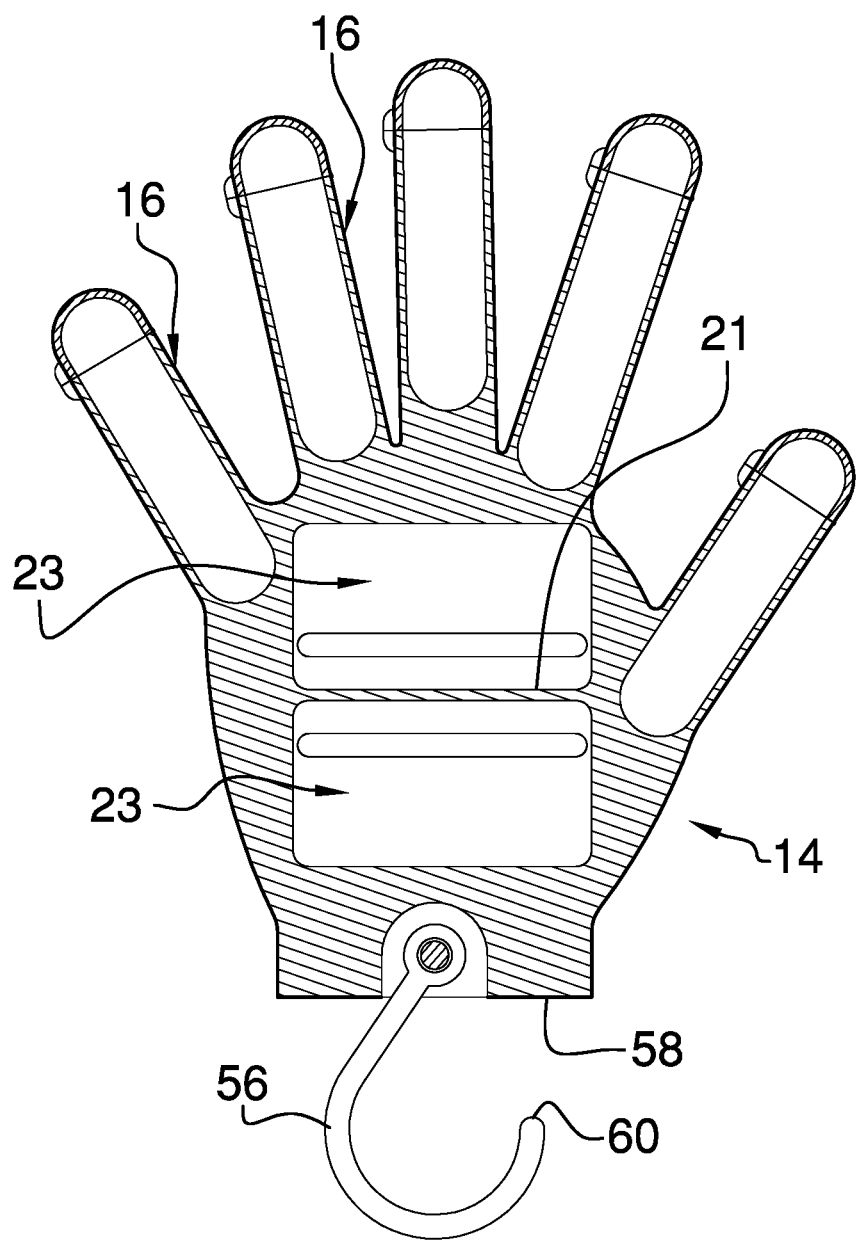
FIG. 5 is a cross sectional view taken along line 5-5 of FIG. 2 of an embodiment of the disclosure.

With reference now to the drawings, and in particular to FIGS. 1 through 5 thereof, a new dispensing device embodying the principles and concepts of an embodiment of the disclosure and generally designated by the reference numeral 10 will be described.

As best illustrated in FIGS. 1 through 5, the feminine product dispensing assembly 10 generally comprises a housing 12 that has a central portion 14 structured to resemble the palm of a human hand and a plurality of finger portions 16 each structured to resemble fingers of a human hand. The central portion 14 is hollow and each of the finger portions 16 is hollow. Additionally, each of the finger portions 16 is fluidly discrete from the central portion 14. The central portion 14 has an opening 18 extending into an interior of the central portion 14 for storing toilet paper 20 and toilet covers 22. A plurality of tampons 24 is positionable in each of the finger portions 16 for storage and the tampons 24 are removable from the finger portions 16. The toilet paper 20 and the toilet covers 22 may be paper products commonly sold by institutional suppliers or the like for public restrooms. As is most clearly shown in FIG. 5, a dividing wall 21 may be positioned within the central portion 14 to define a pair of chambers 23 in the central portion 14.

The central portion 14 has a front wall 26, a back wall 28 and an outer wall 30 extending therebetween. The outer wall 30 is arcuate about a center point of the front wall 26 such that the central portion 14 has a rounded circular shape. The opening 18 in the central portion 14 extends through the front wall 26 of the central portion 14 and the opening 18 has a bounding edge 32. Each of the finger portions 16 is positioned on a top side 34 of the outer wall 30 of the central portion 14 and the finger portions 16 are spaced apart from each other and are distributed along the top side 34. Each of the finger portions 16 has a distal end 36 with respect to the central portion 14 and the distal end 36 of each of the finger portions 16 is open.

A cover 38 is removably attachable to the central portion 14 of the housing 12 to retain the toilet paper 20 and the toilet covers 22 in the central portion 14. The cover 38 has a toilet paper slot 40 that extends therethrough and the toilet paper 20 is extendable therethrough for dispensing. Additionally, the cover 38 has a toilet cover slot 42 extending therethrough and the toilet covers 22 are extendable therethrough for dispensing. A perimeter edge 44 of the cover 38 releasably engages the bounding edge 32 of the opening 18 in the central portion 14 for retaining the cover 38 in place. Each of the toilet paper 20 and the toilet covers 22 may be supplied in a cardboard box similar to a tissue box that can be commonly purchased at institutional suppliers or retail suppliers.

A plurality of lids 46 is each hingedly coupled to a respective one of the finger portions 16. Each of the lids 46 opens or closes the respective finger portion 16 to retain the tampon 24 in the respective finger portion 16. Each of the lids 46 has a bottom edge 48 and an outer surface 50, and the bottom edge 48 is hingedly coupled to the distal end 36 of the respective finger portion 16 at a hinge point 52. The outer surface 50 is convexly arcuate with respect to the distal end 36 of the respective finger portions 16 such that each of the lids 46 has a cup shape.

A magnet 54 is coupled to the housing 12 to magnetically engage a ferromagnetic support surface. The ferromagnetic support surface may be a metal wall of a bathroom stall or other vertical supports surface commonly found in public bathrooms. Additionally, the magnet 54 is positioned on the back wall 28 of the central portion 14 of the housing 12. A hook 56 is coupled to and extends downwardly from the central portion 14 for having an object suspended thereon for storage. The hook 56 is positioned on a bottom side 58 of the outer wall 30 of the central portion 14 and the hook 56 has a distal end 60 with respect to the bottom side 58. Additionally, the hook 56 is curved between the bottom side 58 and the distal end 36 of the hook 56 such that the distal end 36 of the hook 56 is directed toward the bottom side 58.

In use, the cover 38 is removed from the central portion 14 of the housing 12 and the toilet paper 20 and toilet covers 22 are loaded into the central portion 14. The cover 38 is replaced on the central portion 14, the toilet paper 20 is drawn through the toilet paper slot 40 and the toilet covers 22 are drawn through the toilet cover slot 42. Each of the finger portions 16 is loaded with a tampon 24 and the lids 46 on each of the finger portions 16 are closed. In this way the toilet paper 20, the toilet paper covers 22 and the tampons 24 can all be stored in a single location for use by a female in a public bathroom.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A feminine product dispensing assembly being configured to store and subsequently dispense feminine hygiene products in a bathroom stall, said assembly comprising:

a housing having a central portion structured to resemble the palm of a human hand and a plurality of finger portions each structured to resemble fingers of a human hand, said central portion being hollow, each of said finger portions being hollow, each of said finger portions being fluidly discrete from said central portion, said central portion having an opening extending into an interior of said central portion for storing toilet paper and toilet covers, each of said finger portions having a tampon being positioned therein for storage and being removable from said finger portions;

a plurality of lids, each of said lids being hingedly coupled to a respective one of said finger portions, each of said lids opening or closing said respective finger portion wherein each of said lids is configured to retain the tampon in said respective finger portion;

a magnet being coupled to said housing wherein said magnet is configured to magnetically engage a ferromagnetic support surface; and a hook being coupled to and extending downwardly from said central portion wherein said hook is configured to have an object suspended thereon for storage.

2. The assembly according to claim 1, wherein said central portion has a front wall, a back wall and an outer wall extending therebetween, said outer wall being arcuate about a center point of said front wall such that said central portion has a rounded circular shape, said opening in said central portion extending through said front wall of said central portion.

3. The assembly according to claim 2, wherein each of said finger portions is positioned on a top side of said outer wall of said central portion, said finger portions being spaced apart from each other and being distributed along said top side, each of said finger portions having a distal end with respect to said central portion, said distal end of each of said finger portions being open.

4. The assembly according to claim 1, further comprising a cover being removably attachable to said central portion of said housing wherein said cover is configured to retain the toilet paper and the toilet covers in said central portion, said cover having a toilet paper slot extending therethrough wherein said toilet paper slot is configured to have the toilet paper extending therethrough for dispensing, said cover having a toilet cover slot extending therethrough wherein said toilet cover slot is configured to have the toilet covers extending therethrough for dispensing, a perimeter edge of said cover releasably engaging a bounding edge of an opening in said central portion for retaining said cover in place.

5. The assembly according to claim 1, wherein each of said lids has a bottom edge and an outer surface, said bottom edge being hingedly coupled to a distal end of said respective finger portion at a hinge point, said outer surface being convexly arcuate with respect to said distal end of said respective finger portions such that each of said lids has a cup shape.

6. The assembly according to claim 2, wherein said magnet is positioned on said back wall of said central portion of said housing.

7. The assembly according to claim 2, wherein said hook is positioned on a bottom side of said outer wall of said central portion, said hook having a distal end with respect to said bottom side, said hook being curved between said bottom side and said distal end of said hook such that said distal end of said hook is directed toward said bottom side.

8. A feminine product dispensing assembly being configured to store and subsequently dispense feminine hygiene products in a bathroom stall, said assembly comprising:

a housing having a central portion structured to resemble the palm of a human hand and a plurality of finger portions each structured to resemble fingers of a human hand, said central portion being hollow, each of said finger portions being hollow, each of said finger portions being fluidly discrete from said central portion, said central portion having an opening extending into an interior of said central portion for storing toilet paper and toilet covers, each of said finger portions having a tampon being positioned therein for storage and being removable from said finger portions, said central portion having a front wall, a back wall and an outer wall extending therebetween, said outer wall being arcuate about a center point of said front wall such that said central portion has a rounded circular shape, said opening in said central portion extending through said front wall of said central portion, said opening having a bounding edge, each of said finger portions being positioned on a top side of said outer wall of said central portion, said finger portions being spaced apart from each other and being distributed along said top side, each of said finger portions having a distal end with respect to said central portion, said distal end of each of said finger portions being open;

a cover being removably attachable to said central portion of said housing wherein said cover is configured to retain the toilet paper and the toilet covers in said central portion, said cover having a toilet paper slot extending therethrough wherein said toilet paper slot is configured to have the toilet paper extending therethrough for dispensing, said cover having a toilet cover slot extending therethrough wherein said toilet cover slot is configured to have the toilet covers extending therethrough for dispensing, a perimeter edge of said cover releasably engaging said bounding edge of said opening in said central portion for retaining said cover in place;

a plurality of lids, each of said lids being hingedly coupled to a respective one of said finger portions, each of said lids opening or closing said respective finger portion wherein each of said lids is configured to retain the tampon in said respective finger portion, each of said lids having a bottom edge and an outer surface, said bottom edge being hingedly coupled to said distal end of said respective finger portion at a hinge point, said outer surface being convexly arcuate with respect to said distal end of said respective finger portions such that each of said lids has a cup shape;

a magnet being coupled to said housing wherein said magnet is configured to magnetically engage a ferromagnetic support surface, said magnet being positioned on said back wall of said central portion of said housing; and a hook being coupled to and extending downwardly from said central portion wherein said hook is configured to have an object suspended thereon for storage, said hook being positioned on a bottom side of said outer wall of said central portion, said hook having a distal end with respect to said bottom side, said hook being curved between said bottom side and said distal end of said hook such that said distal end of said hook is directed toward said bottom side.

* * * * *